United States Patent

Anglerot et al.

Patent Number: 5,447,709
Date of Patent: Sep. 5, 1995

[54] PROCESS FOR THE SYNTHESIS OF ZEOLITES BELONGING TO THE FAUJASITE STRUCTURAL FAMILY

[75] Inventors: Didier Anglerot, Lons; Béatrice Féron, Pau; Jean-Louis Guth, Brunstatt, all of France

[73] Assignee: Societe Nationale Elf Aquitaine, Courbevoie, France

[21] Appl. No.: 142,221

[22] Filed: Oct. 25, 1993

[30] Foreign Application Priority Data

Oct. 26, 1992 [FR] France ................ 92 12695

[51] Int. Cl.$^6$ ............................. C01B 39/20
[52] U.S. Cl. ................ 423/702; 423/706; 423/DIG. 21; 502/79
[58] Field of Search ........... 423/702, 704, DIG. 21, 423/706; 502/79

[56] References Cited

U.S. PATENT DOCUMENTS

| | | | |
|---|---|---|---|
| 4,714,601 | 12/1987 | Vaughan | 423/DIG. 21 X |
| 5,098,686 | 3/1992 | Delprato et al. | 423/DIG. 21 X |
| 5,158,757 | 10/1992 | Deloprato et al. | 423/709 |
| 5,192,520 | 3/1993 | Delprato et al. | 423/72 |
| 5,273,945 | 12/1993 | Courieres et al. | 502/79 X |
| 5,393,511 | 2/1995 | Delprato et al. | 423/718 |

Primary Examiner—Mark L. Bell
Assistant Examiner—David Sample
Attorney, Agent, or Firm—Burgess, Ryan and Wayne

[57] ABSTRACT

Process for the synthesis of faujasite, having a Si/Al ratio greater than 1 and which can exceed 3, in the presence of a structuring agent consisting of at least one carbonaceous macrocycle having 10 to 24 atoms per ring and containing heteroatoms chosen from oxygen, nitrogen, sulphur or silicon, the macrocycle being introduced into the reaction medium in the form of a crude synthetic sodium complex.

11 Claims, No Drawings

PROCESS FOR THE SYNTHESIS OF ZEOLITES BELONGING TO THE FAUJASITE STRUCTURAL FAMILY

BACKGROUND OF THE INVENTION

1. Field of the Invention

The invention relates to a process for the synthesis of zeolites belonging to the faujasite structural family.

2. Background Art

Zeolites are crystalline tectosilicates. The structures consist of assemblages of $TO_4$ tetrahedra forming a three-dimensional framework by the sharing of oxygen atoms. In zeolites of aluminosilicate type, which are the most common, T represents the tetravalent silicon and the trivalent aluminium. The abovementioned three-dimensional framework has cavities and channels which have molecular sizes and receive the cations which compensate for the charge deficiency related to the presence of trivalent aluminium in the $TO_4$ tetrahedra, the cations generally being exchangeable.

Generally, the composition of the zeolites can be represented by the empirical formula ($M_{2/n}$ O; $Y_2O_3$; $xZO_2$) in the dehydrated and calcined form. In this formula, Z and Y respectively denote the tetravalent and trivalent elements of the $TO_4$ tetrahedra, M represents an electropositive element with a valency n, such as an alkali metal or alkaline-earth metal and constitutes the exchangeable balancing cation, and x is a number which can vary from 2 to theoretically infinity, in which case the zeolite is a silica.

Each type of zeolite has a distinct microporous structure. The variation in the sizes and shapes of the micropores from one type to another leads to changes in the absorbing properties. Only molecules having certain sizes and shapes are capable of entering into the pores of a specific zeolite. Due to their notable characteristics, zeolites are very particularly suited to the purification or the separation of gaseous or liquid mixtures such as, for example, the separation of hydrocarbons by selective adsorption.

The chemical composition, in particular the nature of the elements present in the $TO_4$ tetrahedra and the nature of the exchangeable balancing cations, is also a significant factor which is involved in the adsorption selectivity and especially in the catalytic properties of these products. They are used as catalysts or catalyst supports in cracking, reforming and generally in modifying hydrocarbons, as well as in the synthesis of many molecules.

Many zeolites exist in nature: these are aluminosilicates, the availability and properties of which do not always correspond to the requirements of industrial applications. For this reason, the search for products having novel properties has led to the synthesis of a great variety of zeolites essentially of aluminosilicate type. Among the many examples of this type, it is possible to point out zeolite A (U.S. Pat. No. 2,882,243), zeolite X (U.S. Pat. No. 2,882,244), zeolite Y (U.S. Pat. No. 3,130,007), zeolite L (FR-A-1,224,154), zeolite T (FR-A-1,223,775), zeolite ZSM (U.S. Pat. No. 3,702,886), zeolite ZSM12 (U.S. Pat. No. 3,832,449) and zeolite ZSM4 (EP-A- 0,015,132).

Zeolites of the faujasite structural family are characterized by a three-dimensional framework structure which can be described from the assemblage of units called cube-octahedra. Each of these units consists of 24 tetrahedra containing the elements Si and Al and bridged by oxygen according to the principle described above. In the cube-octahedron, the tetrahedra are joined so as to form eight rings containing six tetrahedra and six rings containing four tetrahedra. Each cube-octahedron is connected in tetrahedral coordination across four rings containing six tetrahedra to four neighbouring cube-octahedra.

It is convenient, in order to show the relationships which unite the various members of the structural family, to consider the structural planes in which the cube-octahedra are arranged at the vertices of a plane network of hexagons. Each cube-octahedron is thus connected to three neighhours in the structural plane.

The fourth bonding direction is directed alternately on either side of the structural plane and makes it possible to connect the cube-octahedra between neighbouring and parallel structural planes.

Depending on the relative arrangements of these structural planes with respect to one another, it is possible to obtain:

sequences of three distinct structural planes ABCABC . . . corresponding to a structure of cubic symmetry, sequences of two distinct structural planes ABAB . . . corresponding to a structure of hexagonal symmetry, more complex sequences which can be regular or irregular.

All the solids belonging to the faujasite structural family are polytypes and have interconnected channels with a diameter of approximately 0.8 nm. Thus faujasite is a natural zeolite whose structure corresponds to the stacking of three distinct structural planes ABC corresponding to a structure of cubic symmetry. It is possible to obtain, by synthesis from a sodium aluminosilicate gel, compounds of the same structure as faujasite, the said compounds being called zeolites X when the Si/Al ratio of the number of silicon atoms to the number of aluminium atoms is between 1 and 1.5 and zeolites Y when the said Si/Al ratio is greater than 1.5.

The general process for the synthesis of zeolites of the faujasite structural family consists of a hydrothermal crystallization of aluminosilicate gels of specific compositions containing a structuring agent, which can be a metal cation and optionally a cation such as tetraethylammonium.

This synthesis has its limits. It does not make it possible to obtain either faujasites having Si/Al ratios greater than 3 or virtually pure hexagonal faujasites. In fact, the faujasites obtained by this process have a cubic structure or else exist in the form of mixtures of cubic and hexagonal shapes.

French Patent 2,638,444 from Elf Aquitaine describes a process which makes it possible to obtain by direct synthesis faujasites whose Si/Al ratio is greater than 3.

These more acidic faujasites are obtained by a process using carbonaceous macrocycles containing heteroatoms chosen from oxygen, nitrogen or sulphur.

The use of these macrocycles makes it possible to direct the synthesis towards the production of cubic or hexagonal faujasites or a mixture of the two structures.

In fact, by using as structuring agent macrocycles having 10 to 17 atoms per ring, the cubic faujasite is obtained, whereas structuring agents containing 18 to 24 atoms in their ring direct the synthesis towards the hexagonal polytype.

In this process, the macrocycles are used in the purified form. Their purification requires many distillation and chromatographic separation stages.

SUMMARY OF THE INVENTION

We have now found a simplified, and therefore more economical, process for the preparation of faujasites containing a high Si/Al ratio.

The process for the synthesis of faujasites having a Si/Al ratio greater than 1 and which can exceed 3, according to the invention, consists in preparing a reaction mixture having a pH greater than 10 and containing water, a source of tetravalent silicon, a source of trivalent aluminium, a source of hydroxide ions in the form of a strong inorganic or organic base and a structuring agent consisting of at least one carbonaceous macrocycle having 10 to 24 atoms per ring and containing heteroatoms chosen from oxygen, nitrogen, sulphur or silicon, in the proportions which make possible the crystallization into a compound of the faujasite structural family, in maintaining the gel obtained at a temperature not greater than 150° C. and under autogenous pressure for a period of time sufficient to carry out the crystallization of the faujasite precursor consisting of the faujasite trapping the structuring agent and in subjecting the precursor to a calcination in order to the structuring agent and to produce the faujasite and it is characterized in that the carbonaceous macrocycle used as structuring agent is introduced into the reaction medium in the form of a crude synthetic sodium complex.

DESCRIPTION OF THE PREFERRED EMBODIMENTS

Advantageously, the amount of structuring agent (St) present in the reaction mixture is such that the $St/Al^{III}$ molar ratio may range from 0.1 to 4 and preferably from 0.1 to 1.

The macrocycles containing between 10 and 17 atoms lead to cubic faujasite. Hexagonal faujasite is obtained using macrocycles containing at least 18 atoms provided that the $Na_2O/Al_2O_3$ molar ratio is adjusted to between 1.4 and 3.5 according to the $SiO_2/Al_2O_3$ ratio. Thus:

for $SiO_2/Al_2O_3=7$, $Na_2O/Al_2O_3$ will be taken between 1.4 and 2.4 for $SiO_2/Al_2O_3=10$, $Na_2O/Al_2O_3$ will be taken between 1.8 and 2.8 for $SiO_2/Al_2O_3=15$, $Na_2O/Al_2O_3$ will be taken between 2.2 and 3.5

The sodium complex of the carbonaceous macrocycle can be synthesized by any known process.

The most commonly used macrocycles are crown ethers. The synthesis of crown ethers generally uses glycol ethers, according to the general reaction:

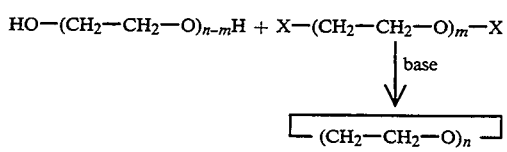

where X is generally chosen from OH, tosylate or halide groups and where n ranges from 4 to 8 and m from 0 to 4. If X=OH, the cyclization requires the presence of a reagent such as tosyl chloride.

The cyclooligomerization of ethylene oxide can also be envisaged.

For the synthesis of 1,4,7,10,13,16-hexaoxacyclooctadecane ("18-crown-6" crown ether), derivatives of triethylene glycol are generally used.

A simple process consists in cyclizing triethylene glycol in the presence of para-toluenesulphonyl chloride and sodium hydroxide. The crown ether 18-crown-6 is obtained in the tosylate form of its sodium complex.

In place of two triethylene glycol molecules, it is possible to use one molecule of hexaethylene glycol.

The same product can be obtained by cyclizing triethylene glycol and triethylene glycol ditosylate in the presence of sodium hydroxide. Of course, other pairs of diols and of ditosylates can be used, especially diethylene glycol and tetraethylene glycol ditosylate.

In place of the tosylates, it is possible to use other leaving groups, especially halides, particularly chlorides.

Thus, 18-crown-6 can be obtained, for example, from triethylene glycol and the corresponding dichloride in the presence of sodium hydroxide.

The crude synthetic sodium complex of the crown ether 18-crown-6 obtained after evaporation of the solvent exists in the form of an oil. This oil can be used directly in the hydrothermal synthesis of faujasite. However, it may be preferable to separate the unreacted starting materials and the reaction by-products.

Among the sources of tetravalent silicon $Si^{IV}$ which can be used in the preparation of the reaction mixture intended to form the aluminosilicate gel, there may be mentioned finely divided solid silicas in the form of hydrogels, aerogels or colloidal suspensions, water-soluble silicates such as alkali metal silicates such as sodium silicate, hydrolysable silicic esters such as the tetraalkyl orthosilicates of formula $Si(OR)_4$ in which R denotes a $C_1$ to $C_4$ alkyl such as methyl and ethyl. The silicon source is used in the form of a true aqueous solution, in the case of water-soluble silicates, or else of an aqueous suspension which can be colloidal, in the case of finely divided silicas.

Aluminium salts, such as sulphate, nitrate, chloride, fluoride or acetate, aluminium oxides and hydroxides, aluminates and especially alkali metal aluminates such as sodium aluminate, and aluminium esters such as the aluminium trialkoxides of formula $Al(OR)_3$ in which R denotes a $C_1$ to $C_4$ alkyl radical such as methyl, ethyl or propyl are suitable as $Al^{III}$ trivalent aluminium sources.

The source of hydroxide ions is chosen from strong inorganic bases, especially hydroxides of the alkali metals of Group IA of the Periodic Classification of the Elements and hydroxides of the alkaline-earth metals Ca, Sr and Ba, and strong organic bases, especially quaternary ammonium hydroxides, the preference going to inorganic bases and especially to sodium hydroxide, NaOH.

The reaction mixture intended to form the aluminosilicate gel can also contain cations $M^{n+}$ of at least one metal M, of valency n, other than the metals whose hydroxides are strong bases, in an overall amount such that the $M^{n+}/Al^{III}$ molar ratio is not greater than 0.4 and preferably not greater than 0.3. The said cations $M^{n+}$ are introduced into the said reaction mixture in the form of salts such as sulphates, nitrates, chlorides or acetates or yet again in the form of oxides. As examples of such cations, mention may in particular be made of $Co^{++}$, $Cd^{++}$, $Mg^+$ and $Ag^+$.

In order to form the reaction mixture intended to form the aluminosilicate gel, the structuring agent, in the form of the crude synthetic sodium complex, is introduced into water. In the event of formation of a precipitate or of separation of an organic phase, it is possible to separate this precipitate or this phase from the aqueous phase.

A basic aqueous solution containing a strong base, $M^{n+}$ cations, if they are used, an aqueous solution of the trivalent aluminium source and an aqueous solution or a suspension, colloidal or noncolloidal, of the tetravalent silicon source are added, at room temperature and in any order, to the aqueous solution of the structuring agent. It is, of course, necessary to take into account, in the calculation of the strong base to be added, the free base content contained in the aqueous solution of the structuring agent.

It is possible to introduce seeds of crystals of hexagonal faujasite or of polytype into this mixture.

The reaction mixture can be subjected to a maturing, generally at room temperature, for approximately 6 hours to 20 days, preferably from 6 hours to 6 days. In general, a maturing of approximately 24 hours is sufficient.

The crystallization of the aluminosilicate gel is carried out by heating the reaction mixture at a temperature not greater than 150° and preferably ranging from 90° to 120° and under a pressure corresponding at least to the aueogenous pressure of the reaction mixture forming the gel. The heating time required for the crystallization depends on the gel and on the crystallization temperature. It is generally between 2 hours and 15 days.

These crystals obtained are crystals of the zeolite precursor, trapping the structuring agent in its pores and cavities. After separation from the reaction mixture by filtration, the crystals are washed with distilled water until wash liquors are obtained whose pH is less than 9. The washed crystals are then dried in an oven at a temperature between 50° and 100° C. and preferably at approximately 70° C.

The zeolite is obtained from the crystals of the precursor by calcination at a temperature greater than 300° C. and preferably between 400° and 700° C. for a time sufficient to remove the structuring agent.

The zeolites prepared by the process according to the invention have Si/Al ratios greater than 1 and which can exceed 3. They are of faujasite type and have a structure of cubic or hexagonal symmetry.

The faujasites obtained by the process according to the invention are suitable as selective adsorbents of molecules whose sizes are less than 0.8 nm, or also, after having been subjected to exchange reactions with various cations, as catalysts or catalyst components which can be used in reactions for the catalytic conversion of organic compounds and in particular of hydrocarbon compounds.

The following examples illustrate the invention without, however, limiting it:

Examples

Example 1

Synthesis of the 18C6-NaOTs complex from TEG ditosylate and TEG a) Synthesis of triethylene glycol (TEG) ditosylate 80 g (2 mol) of sodium hydroxide dissolved in 400 ml of water and 105.12 g (0.70 mol) of triethylene glycol dissolved in 400 ml of THF are placed in a 4 l round-bottomed flask stirred with a glass shaft equipped with an anchor and cooled with a water/ice mixture.

A solution of 243 g of p-toluenesulphonyl chloride (1.3 mol) in 400 ml of THF is added dropwise via a dropping funnel (over a period of 2 hours).

The mixture is allowed to stir for a further 2 hours after the end of the addition and then 1 liter of a water-+ice mixture is poured, which has the effect of precipitating the ditosylate which is filtered off and dried. The yield of the crude product is 83%. The NMR spectrum is entirely in accordance with that expected.

b) Synthesis of the complex.

15.017 g of TEG (0.1 mol) are dissolved in a suspension of 8 g of NaOH (0.2 mol), ground to a powder, in 900 ml of THF.

The previously synthesized ditosylate (0.1 mol–45.8 g) is then added. The mixture is brought to reflux with stirring for 2 hours, cooled, filtered and then the solvent is evaporated.

Example 2

Synthesis of 18 -C- 6 -NaCl complex from TEG dichloride and TEG 112.5 g of triethylene glycol (0.75 mol) and 600 ml of THF are put in a 3 liter round-bottomed flask equipped with a stirrer shaft, a reflux condenser and a dropping funnel. Stirring is begun and 70 ml of an aqueous sodium hydroxide (66.4 g–1.65 mol) solution are added.

After stirring for 15 min, a solution of 3,6-dioxa-1,8-dichlorooctane (140.3 g–0.75 mol) (=dichlorinated triethylene glycol) in 100 ml of THF is added in a single charge. The mixture is heated at reflux and stirred vigorously for 18 hours. The solution is cooled and the THF evaporated under reduced pressure. The resulting chestnut slurry is diluted with dichloromethane (500 ml) and filtered (the sodium chloride formed beside the 18-crown-6-NaCl complex is thus removed) and the solvent is then evaporated.

Example 3

Synthesis of the 18-C-6-NaOTs complex from TEG 35.5 g (0.887 mol) of sodium hydroxide, ground to a powder, are suspended in 1 liter of THF in a 4 liter round-bottomed flask equipped with a reflux condenser, a dropping funnel and a stirrer shaft.

Moreover, 33.37 g of triethylene glycol (0.222 mol) are mixed with 42.36 g of p-toluenesulphonyl chloride (0.222 mol) in 1liter of THF. This mixture is placed in the dropping funnel and added to the suspension at reflux over 5 hours. The brownish mixture obtained is cooled and the white precipitate formed (TsONa+-NaCl) is filtered, and then the solvent is evaporated (on a rotary evaporator).

Example 4

Synthesis of faujasite with, the complex of Example 3

First of all an aluminosilicate gel was prepared by carrying out the reaction as follows in a receiver of suitable capacity, the contents of the said receiver being maintained under stirring throughout the whole of the operation. 8.9 parts of water, then 0.58 part of sodium hydroxide NaOH and, after the sodium hydroxide had dissolved, 2.52 parts of the product of Example 3 were introduced into the receiver.

1 part of a sodium aluminate containing 56% of $Al_2O_3$ and 37% of $Na_2O$ were then added to the contents of the receiver and the reaction mixture was heated gently in order to completely dissolve the aluminate. After returning to room temperature, 8.2 parts of a colloidal suspension of silica containing 40% of SiO$_2$ and 60% of water were then introduced into the receiver.

An aluminosilicate gel was thus obtained whose molar composition, with respect to one mol of Al$_2$O$_3$, was the following:

10 SiO$_2$; 1 Al$_2$O$_3$; 2.4 Na$_2$O; 1 St; 140 H$_2$O.

0.045 part of seeds consisting of a hexagonal faujasite synthesized beforehand, the crystals of which have been ground, was added to this gel, before maturing.

The gel obtained was subjected to a maturing at room temperature for 24 hours in a closed receiver.

The matured gel was then placed in an autoclave and maintained at 110° C. in the latter for 144 hours to form a crystalline product. The crystals formed were separated from the reaction medium by filtration, then washed with distilled water until the wash liquors were low in basicity (pH less than 9) and finally dried at approximately 60° C. in an oven. They exist in the form of hexagonal platelets of approximately 3 μm. The dried crystals were then calcined at 600° C. for 4 hours in order to remove the molecules of the crown ether used as structuring agent and to obtain the zeolite.

The X-ray diffraction spectrum of this sample is similar to that of EMT.

Example 5

Synthesis of faujasite with the complex of Example 1

6.9 g of the product of Example 1 are dissolved in 24.3 g of water. The precipitate is separated by filtration and then 1.34 g of sodium hydroxide, 2.7 g of aluminate and 22.5 g of Ludox are added to the filtrate to obtain a gel whose molar composition is the following:

10 SiO$_2$; 1 Al$_2$O$_3$; 2.2 Na$_2$O; 1 St; 140H$_2$O

After maturing for 24 hours at room temperature, the aluminosilicate gel is maintained at 110° C. for 6 days to form a crystalline product. The crystals formed are separated from the reaction medium by filtration, then washed with distilled water until the wash liquors are low in basicity and finally dried at approximately 60° C.

The diffraction spectrum of this product is identical to that of EMT.

Example 6

Synthesis of faujasite with the complex of Example 2.

1.77 parts of the product of Example 2 are dissolved in 162 g of water and the solution, the pH of which is basic, is neutralized with concentrated hydrochloric acid until pH=7.0.84 part of sodium hydroxide, 1 part of sodium aluminate (containing 56% Al$_2$O$_3$ and 37% Na$_2$O) and 8.24 parts of a colloidal silica suspension containing 40% SiO and 60% water are then added.

The aluminosilicate gel thus prepared has the following molar composition:

10 SiO$_2$.1 Al$_2$O$_3$.2.9 Na$_2$O.1 St .140 H$_2$O

The gel, matured for 24 hours at room temperature in the presence of seeds (0.044 part), is maintained at 115° C. for 65 hours, after which the crystals are separated by filtration, washed and dried.

The diffractogram of this sample is similar to that of a cubic faujasite.

We claim:

1. Process for the synthesis of faujasites having a Si/Al ratio greater than 1 which comprises preparing a reaction mixture having a pH greater than 10 and containing water, a source of tetravalent silicon, a source of trivalent aluminium, a source of hydroxide ions in the form of a strong inorganic or organic base and a structuring agent consisting of at least one carbonaceous macrocycle having 10 to 24 atoms per ring and containing heteroatoms chosen from oxygen, nitrogen, sulphur or silicon, in the proportions which make possible the crystallization into a compound of the faujasite structural family, in maintaining the gel obtained at a temperature not greater than 150° C. and under autogenous pressure for a period of time sufficient to carry out the crystallization of the faujasite precursor consisting of the faujasite trapping the structuring agent and in subjecting the precursor to a calcination in order to destroy the structuring agent and to produce the faujasite and being characterized in that the carbonaceous macrocycle used as structuring agent is introduced into the reaction medium in the form of a synthetic sodium complex.

2. Process according to claim 1, wherein the amount of structuring agent (St) present in the mixture is such that the St/Al$^{III}$ molar ratio may range from 0.1 to 4.

3. Process according to claim 1 wherein the structuring agent is a macrocycle containing 10 to 17 atoms.

4. Process according to claim 1 wherein the structuring agent is a macrocycle containing at least 18 atoms, and in that the Na$_2$O/Al$_2$O$_3$ molar ratio is between 1.4 and 3.5.

5. Process according to claims 1 wherein the sodium complex is a crown ether.

6. Process according to claim 5, wherein the crown ether containing between 10 and 24 atoms is obtained by the cyclization reaction,

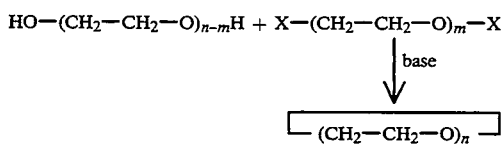

where X is chosen from OH, tosylate or halide groups, where n ranges from 4 to 8 and m from 0 to 4.

7. Process according to claim 5, wherein the crown ether is obtained by cyclizing ethylene oxide.

8. Process according to claim 5, wherein the crown ether is 1,4,7,10,13,16-hexaoxacyclooctadecane (18-crown-6).

9. Process according to claim 8, wherein 18-crown-6 is obtained by cyclizing triethylene glycol in the presence of sodium hydroxide and of p-toluenesulphonyl chloride.

10. Process according to claim 8, wherein 18-crown-6 is obtained by cyclizing triethylene glycol and triethylene glycol ditosylate in the presence of sodium hydroxide.

11. Process according to claim 1, wherein the amount of structuring agent (St) present in the mixture is such that the St/Al$^{III}$ molar ratio may range from 0.1 to 1.

* * * * *